United States Patent
Pentecost et al.

(10) Patent No.: US 11,497,840 B2
(45) Date of Patent: Nov. 15, 2022

(54) INDIRECT DRAIN FLUSH SYSTEM FOR DIALYSIS EFFLUENT

(71) Applicant: PHS Solutions LLC., Ludlow Falls, OH (US)

(72) Inventors: Randy J. Pentecost, Central City, KY (US); Bryan S. Hall, Salyersville, KY (US); Fred A. Sink, Ludlow Falls, OH (US)

(73) Assignee: PHS SOLUTIONS LLC., Ludlow Falls, OH (US)

( * ) Notice: Subject to any disclaimer, the term of this patent is extended or adjusted under 35 U.S.C. 154(b) by 0 days.

(21) Appl. No.: 17/680,604

(22) Filed: Feb. 25, 2022

(65) Prior Publication Data

US 2022/0265909 A1    Aug. 25, 2022

Related U.S. Application Data

(60) Provisional application No. 63/153,509, filed on Feb. 25, 2021.

(51) Int. Cl.
*A61M 1/16* (2006.01)

(52) U.S. Cl.
CPC ........ *A61M 1/1662* (2014.02); *A61M 1/1666* (2014.02); *A61M 2205/127* (2013.01); *A61M 2205/18* (2013.01); *A61M 2205/3337* (2013.01); *A61M 2205/3351* (2013.01); *A61M 2205/3355* (2013.01); *A61M 2205/7563* (2013.01)

(58) Field of Classification Search
CPC .............. A61M 1/1662; A61M 1/1666; A61M 2205/127; A61M 2205/18; A61M 2205/3337; A61M 2205/3351; A61M 2205/3355; A61M 2205/7563
See application file for complete search history.

(56) References Cited

U.S. PATENT DOCUMENTS 10,426,882 B2    10/2019 Kelly et al.

OTHER PUBLICATIONS

BPF Pipes Group, New Guidance Helps Clarify Use of Domestic Air Admittance Valves, https://www.bpf.co.uk/article/new-guidance-helps-clarify-use-of-domestic-air-admittance-valves-1362.aspx, Feb. 8, 2021, 2 pages, UK.
Balkan Sewer & Drain Cleaning, Inc., An airgap prevents contamination to your water and piping system, https://www.balkandraincleaning.com/air-gap-plumbing-pipe-systems/, Feb. 8, 2021, 6 pages, USA.
plumbingsupply.com, How & Why Air Admittance Valves Are Used, https://www.plumbingsupply.com/how-and-why-air-admittance-valves-are-used.html, Feb. 8, 2021, 2 pages, USA.

*Primary Examiner* — Dirk R Bass
(74) *Attorney, Agent, or Firm* — Standley Law Group LLP; Stephen Grant; Bryan Finneran

(57) ABSTRACT

An indirect drain flush system incorporating hot water to facilitate the transport of kidney dialysis effluent to wastewater treatment facilities is provided. Heated water is discharged into a waste line through an air gap, and the heated water increases the molecular interchange of fatty substances in the dialysis effluent, decreasing the viscosity of those fatty substances and preventing them from coagulating or crystalizing on pipes and drains. An air admittance valve may prevent negative pressure from building up within the system.

20 Claims, 6 Drawing Sheets

Prior Art

INDIRECT DRAIN FLUSH SYSTEM FOR DIALYSIS EFFLUENT

CROSS-REFERENCE TO RELATED APPLICATIONS

This application is entitled to benefit of a right of priority from U.S. Provisional Application No. 63/153,509 filed on Feb. 25, 2021. The content of that application is incorporated by reference as if fully recited herein.

TECHNICAL FIELD

Embodiments of the present disclosure relate to an indirect drain flush system for dialysis effluent. More particularly, embodiments relate to an indirect drain flush system wherein heated water facilitates the transport of kidney dialysis effluent to one or more wastewater treatment facilities.

BACKGROUND

Kidney failure and reduced kidney function have been treated with a process called "dialysis" or "kidney dialysis." Dialysis removes waste, toxins, excess salt and excess water from the body that otherwise would have been removed by normal functioning kidneys. The waste, toxins, excess salt and excess water are transferred from blood to a body-temperature dialysis solution called "dialysate" by filter and membrane action of dialysis equipment. The dialysate containing waste, toxins, excess salt and excess water, or "spent dialysate" or "dialysis effluent" is discharged into a waste line by an effluent pipe, tube or hose. The dialysate should not contain blood, as treated blood should be recirculated to the patient. The spent dialysate comprises a high concentration of lipids and lipoproteins such as cholesterol (collectively "fatty substances") removed from the blood. Lipids are hydrophobic, and lipoproteins are amphipathic, thus these organic molecules have a tendency to coagulate into large, viscous masses, or crystalize on sewage drains and pipe walls, especially after the initially body-temperature spent dialysate mixes with cooler liquids, such as room temperature wastewater. Rapid cooling of the spent dialysate leads to reduced molecular interchange of lipid and lipoprotein particles, causing said particles to coagulate or crystalize.

The formation of viscous masses and crystallization of fatty substances on sewage drains and pipe walls is problematic for several reasons. Blockage may occur if a drain opening or pipe contains large enough viscous masses or fouling from crystallized fatty substances such that the flow path of waste water is obstructed. Flow path obstruction could lead to wastewater leakage or flooding caused by high positive water pressure, and related damage to drains and pipes. Additionally, the viscous masses and crystalized fatty substances may attract unwanted organisms, including by way of illustration and not limitation, gnats, and microorganisms, and may cause unpleasant odors. Labor may be required to remove viscous masses and crystalized fatty substances from drains or pipes, and new parts may be required to replace damaged drains or pipes.

The traditional approach to preventing the formation of viscous masses and crystalized fatty substances on drains and pipes leading from a dialysis waste line (tubes, hoses, or piping which transport spent dialysate to a municipal sewage system) is to introduce chemicals to effluent at the end of the dialysis waste line. Specifically, before spent dialysate is discharged from the dialysis waste line to a sewer, the spent dialysate may be mixed with chlorine compounds intended to prevent fatty substances from coagulating or crystalizing. Generally, the chlorine compounds are stored as a liquid in chemical vats, and the liquid may be distributed to the spent dialysate through tubes linked to a motor, the motor controlling the volume and flow rate of the liquid.

Although the traditional approach has reduced the amount of fouling and coagulation of fatty substances in sewage lines leading from dialysis centers, and reduced the presence of certain unwanted organisms and unpleasant odors, there have been numerous issues with this chemical-based approach. Fatty substance buildup, fouling and related blockage are still potential issues for several reasons. With the traditional approach, by the time the spent dialysate reaches a sewage drain at the end of the dialysis waste line, lipids and lipoproteins have already started to coagulate, and large masses of these particles are known to form on or in proximity to the drain irrespective of chlorine compound addition. Additionally, the chemical-based approach has not proven effective at fully preventing coagulation or crystallization in sewage lines leading from dialysis centers to wastewater treatment facilities. With the traditional method, it is very common for dialysis center managers to have to regularly clean coagulated or crystallized fatty substances from drains and pipes. Furthermore, these substances are difficult to remove from sewage lines after the effluent has left the dialysis centers.

Another issue with the traditional approach is that the chlorine compounds added to the spent dialysate may cause other unpleasant odors and pollute the wastewater. Wastewater treatment facilities rely on microbial processes to break down organic compounds and ammonia-based compounds found in very high concentrations in sewage. Chlorine inactivates all types of microorganisms, including bacteria crucial to breaking down the organic and ammonia-based compounds which would otherwise contaminate the water supply if discharged from the wastewater treatment facility.

In view of this, it would be helpful develop an indirect drain flush system wherein heated water, as opposed to chemicals, facilitates the transport of kidney dialysis effluent to one or more wastewater treatment facilities.

SUMMARY

It is an object of the present invention to provide a system and method for facilitating the transport of dialysis effluent to wastewater treatment facilities using heated water to prevent the coagulation of lipids and lipoproteins, or fouling related to the crystallization of lipids and lipoproteins with respect to drains and pipes. Elevating the temperature of the dialysis effluent above its initial temperate of approximately 98° F. increases the molecular interchange of lipid and lipoprotein particles, thus decreasing the viscosity of these fatty substances. With respect to fluids, flow rate is inversely proportional to viscosity, thus dialysis effluent mixed with hot water has a greater flow rate. The elevated flow rate and increased molecular interchange of the lipids and lipoprotein particles prevents those particles from accumulating or crystalizing on pipes or drains. With the present invention, these fatty substances inevitably end up at a wastewater treatment facility, but they are suspended in the wastewater mixture, and are thereafter easily removed by settling, biological and clarification processes. Thus, the issue of point source coagulation and fouling has been resolved.

It is a further objective of the present invention to provide a system and method for facilitating the transport of dialysis effluent to wastewater treatment facilities where chemicals potentially harmful to the water supply need not be added. With the present invention, heated water, preferably from a domestic tap water source, is introduced to the dialysis effluent, but preferably without any added chemicals, such as chlorine. The addition of heated water causing increased molecular interchange of lipids and lipoprotein particles independently resolves the issue of point source coagulation and fouling.

With the above objectives in view, the present invention discloses a system and its corresponding method of an indirect drain flush system for dialysis effluent. In exemplary embodiments of the present invention, spent dialysate or dialysis effluent flows from a dialysis machine to an indirect drain flush system (generally speaking, a drain flush system is indirect if it comprises at least one air gap separating the system from a drain linked to wastewater infrastructure) comprising piping for transporting spent dialysate and mixed effluent. Extending approximately vertically from one or more effluent pipes may be one or more air admittance pipes having air admittance valves facilitating the flow of effluent therein. An air gap between a hot water feed and the dialysis waste line may prevent the backflow of dialysis effluent into the hot water feed.

According to the present invention in one aspect, a time-cycled hot water system controls the volume and flux or flow rate of hot water discharged into the dialysis waste line. In some embodiments, the source of hot water is a domestic hot water supply. In preferred embodiments, one or more components of the indirect drain flush system are linked to an alarm connected to at least one flow meter, the alarm alerting users if there is backup or fouling within the system. The dialysis effluent mixed with heated water ("mixed effluent") may flow from an effluent pipe comprising inspection tubing towards a sewage drain. Lipids and lipoproteins may remain suspended in wastewater thereafter before reaching a wastewater treatment facility.

According to the present invention in another aspect, a portable indirect drain flush system for dialysis effluent is provided. In certain preferred embodiments of the present invention, the component parts are temporarily suspended from, affixed or attached to walls or pipe chases, plumbing walls, or the like ("chase cabinetry") in a dialysis center. Additionally, effluent piping may be temporarily attached to an effluent hose, tube or pipe leading from a dialysis machine. Furthermore, a time cycled-hot water system may be temporarily attached to a domestic hot water supply. Also, component parts may easily be transported between different dialysis treatment centers and reassembled into a working indirect drain flush system.

BRIEF DESCRIPTION OF THE DRAWINGS

Novel features and advantages of the present invention, in addition to those expressly mentioned herein, will become apparent to those skilled in the art from a reading of the following detailed description in conjunction with the accompanying drawings. The present disclosure is illustrated by way of example, and not by way of limitation, in the figures of the accompanying drawings in which like references indicate similar elements. It should be noted that different references to "an" or "one" embodiment in this disclosure are not necessarily to the same embodiment, and such references mean at least one.

DETAILED DESCRIPTION OF EMBODIMENTS

Figure 1:
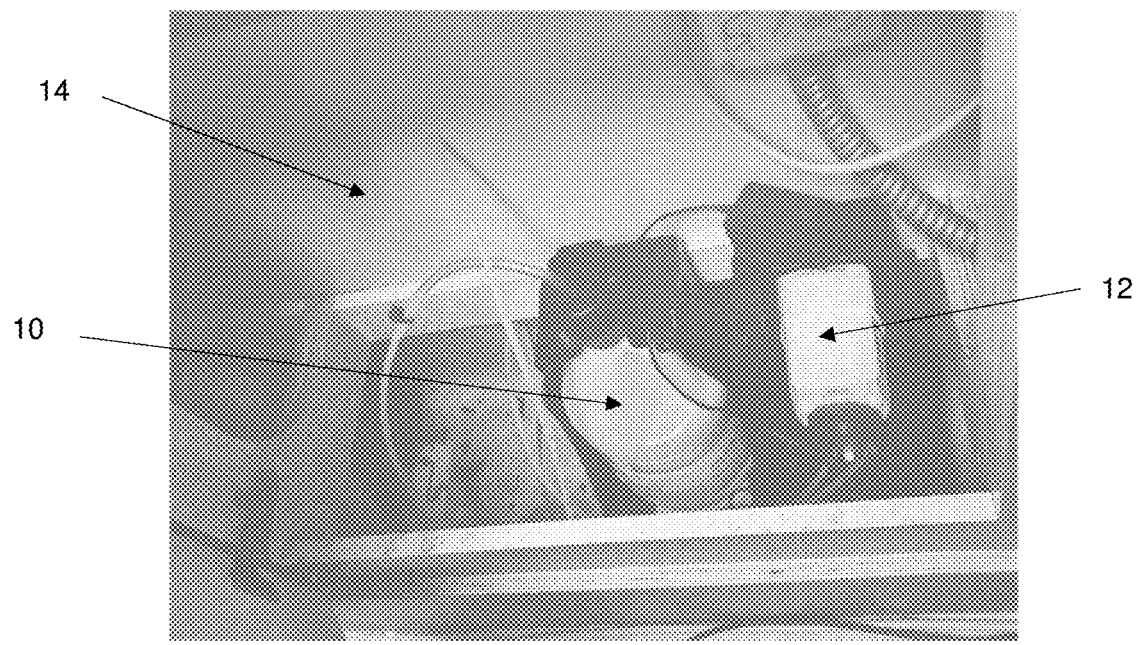
FIG. 1 is a top perspective view of a prior art kidney dialysis effluent treatment apparatus.

FIG. 1 shows a prior art kidney dialysis effluent treatment apparatus 14. Chlorine-based compounds from a chemical vat 10 are introduced to dialysis effluent (not shown) at the end of a dialysis waste line (not shown). The chlorine-based compounds in chemical vat 10 are stored as a liquid. The distribution of the liquid from chemical vat 10 is controlled by a motor 12. The motor 12 controls the volume and flow rate of the liquid being discharged into the effluent.

Figure 2:
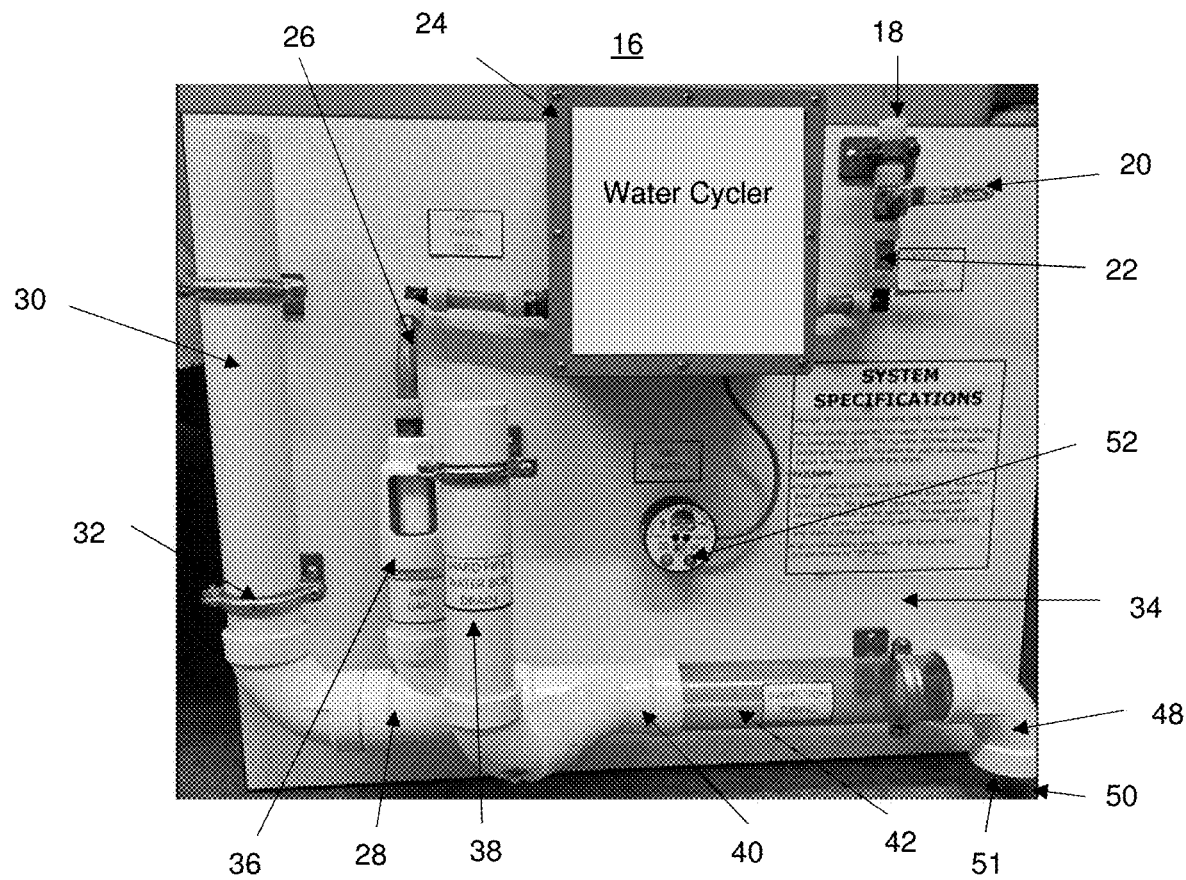
FIG. 2 is a front perspective view of an exemplary indirect drain flush system for dialysis effluent.

FIG. 2 shows an exemplary indirect drain flush system for dialysis effluent ("drain system") 16. The drain system 16 is characterized as "indirect" because it comprises one or more air gaps. In this particular embodiment, a hot water air gap 36 and a release gap 50 positioned between a drain and an opening ("release opening") 51 at the end of the dialysis waste line 28 for discharging mixed effluent are included. The drain system 16 may further comprise hot water pipes 22 where heated water 18 may flow from a hot water supply (not shown) to a water cycler 24, and the flow may be permitted or restricted by a ball valve 20. In the embodiment shown, the water cycler 24 discharges heated water 18 into pipes of a hot water feed 26, and the hot water feed 26 discharges the heated water 18 through the hot water air gap 36 to be received by a dialysis waste line 28.

The dialysis waste line 28 may comprise a raw effluent zone 30 and a mixed effluent zone 40. In exemplary embodiments of the present invention, the mixed effluent zone 40 includes one or more sections of inspection tubing 42. The inspection tubing may be around a foot in length in certain embodiments. The dialysis waste line 28 may be securely attached to a wall 34 by fastened rigid straps 32. Additionally, an air admittance pipe 38 may be attached to the dialysis waste line 28. In the FIG. 2 embodiment, heated water mixed with spent dialysate, or "mixed effluent" is discharged from a 90° elbow pipe 48 over the release gap 50. An alarm 52 connected to the water cycler 24 is also shown. In certain preferred embodiments, PVC is used for the dialysis waste line 28, including the raw effluent zone 30, mixed effluent zone 40 and air admittance pipe 38, and for the fixture defining the hot water air gap 36.

In the FIG. 2 embodiment, spent dialysate (not shown) enters the raw effluent zone 30 and flows towards the mixed effluent zone 40. Heated water 18 flowing from the hot water feed 26 may be discharged through the hot water air gap 36, and then may mix with the spent dialysate to create mixed effluent, which flows through the mixed effluent zone 40 towards the release gap 50. The addition of heated water 18 to the spent dialysate comprising high concentrations of lipids and lipoproteins may cause increased molecular interchange of lipid and lipoprotein particles, which reduces the viscosity of the spent dialysate and prevents fouling and coagulation of fatty substances. In some embodiments, spent dialysate enters the dialysis waste line 28 after the location where heated water 18 is discharged into the dialysis waste line 28, thus a raw effluent zone 30 preceding the hot water air gap 36 is not required. Examples of drain systems without raw effluent zones 30 are shown and described below.

Figure 3:
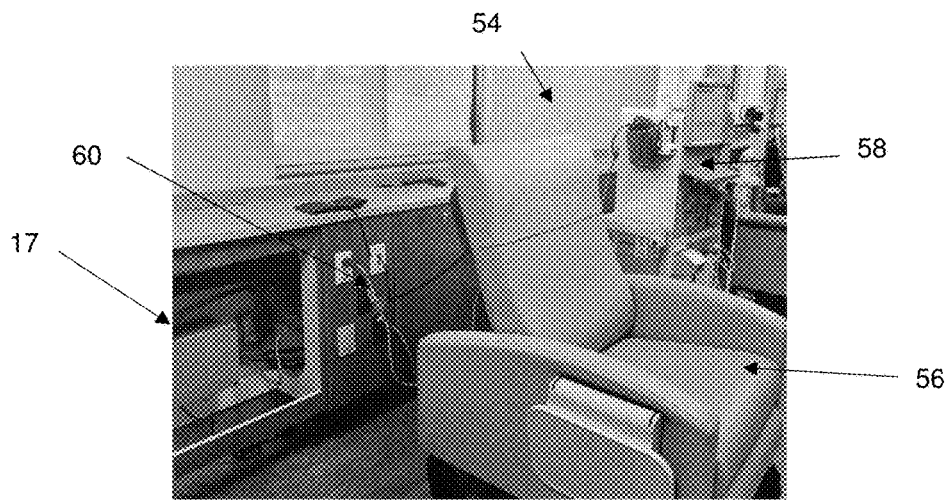
FIG. 3 is a perspective view of a dialysis unit and an exemplary indirect drain flush system for dialysis effluent.

FIG. 3 shows a kidney dialysis unit 54 comprising a chair 56 and a hemodialysis machine 58. The hemodialysis machine 58 may be powered by a power cord 60 meeting the machine's 58 fundamental electrical requirements. Positioned to the rear of the kidney dialysis unit 54 is an exemplary drain system 17. In the embodiments shown and described herein, hemodialysis machines 58 are used by way of example. The present invention is not intended to be limited to the transport of dialysis effluent from hemodialysis. In certain preferred embodiments, exemplary indirect drain flush systems for dialysis effluent may also transport dialysis effluent from hemofiltration therapy, hemodiafiltration, peritoneal dialysis, any other form of dialysis therapy, or any other process where effluent comprises high concentrations of lipids, lipoproteins, or other hydrophobic or amphipathic biochemicals.

Figure 4:
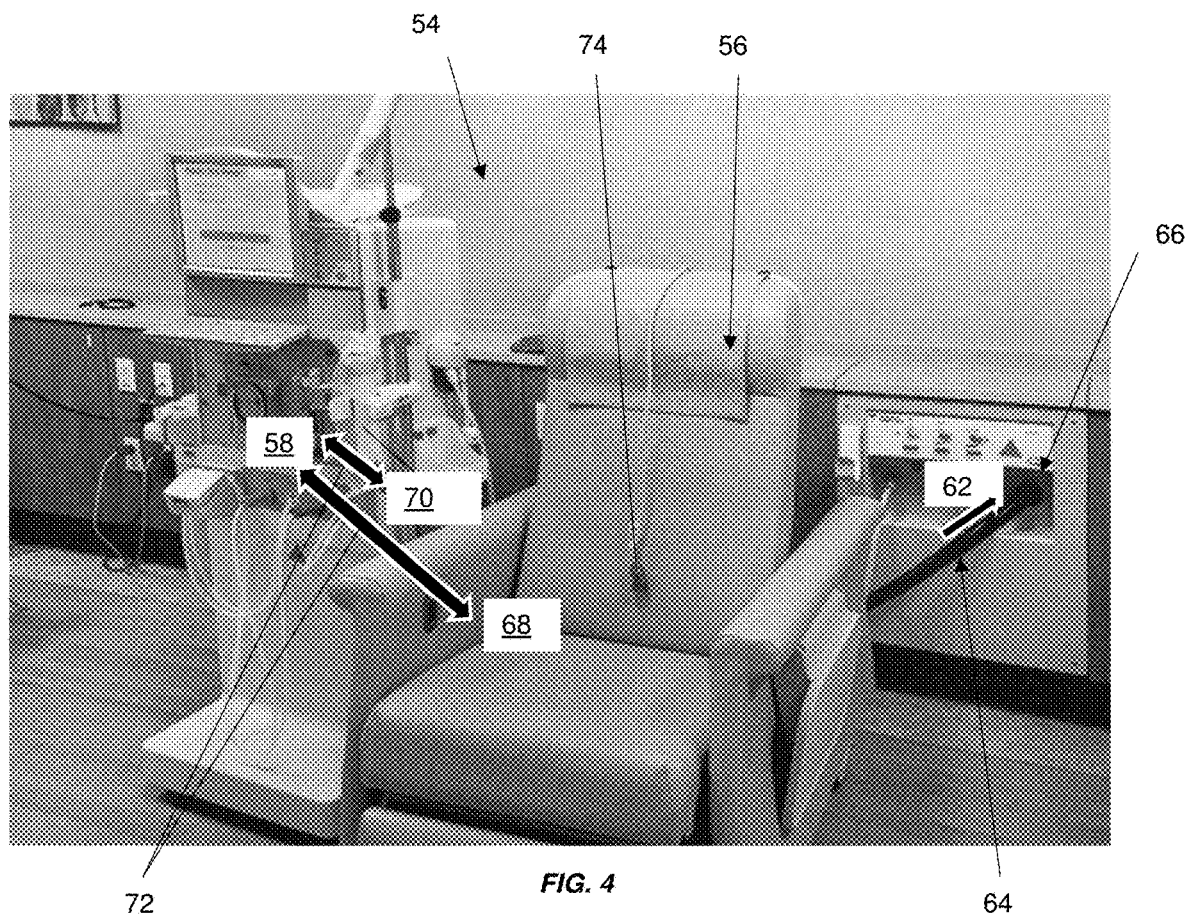
FIG. 4 is a front perspective view of a dialysis unit comprising a chair, dialyzer and hemodialysis machine in fluid connection with an exemplary indirect drain flush system for dialysis effluent.

Referring now to FIG. 4, an exemplary kidney dialysis unit 54 comprising a chair 56, hemodialysis machine 58, and dialyzer 70 of hemodialysis machine 58 is shown. Needles and catheters linked to tubes 74 may be inserted into the patient's 68 veins and arteries to create a blood flow path 72 to and from the hemodialysis machine 58. As blood passes through the dialyzer 70, waste, toxins, excess salt and excess water may be transferred to dialysate by diffusion action of a dialyzer membrane (not shown), and the clean blood may be returned to the patient 68. The spent dialysate 62, which does not contain any blood, may be circulated to the back of the hemodialysis machine 58 and thereafter transported to a drain system (not shown) through an effluent hose 64 which may connect to the drain system through an aperture 66.

Figure 5:
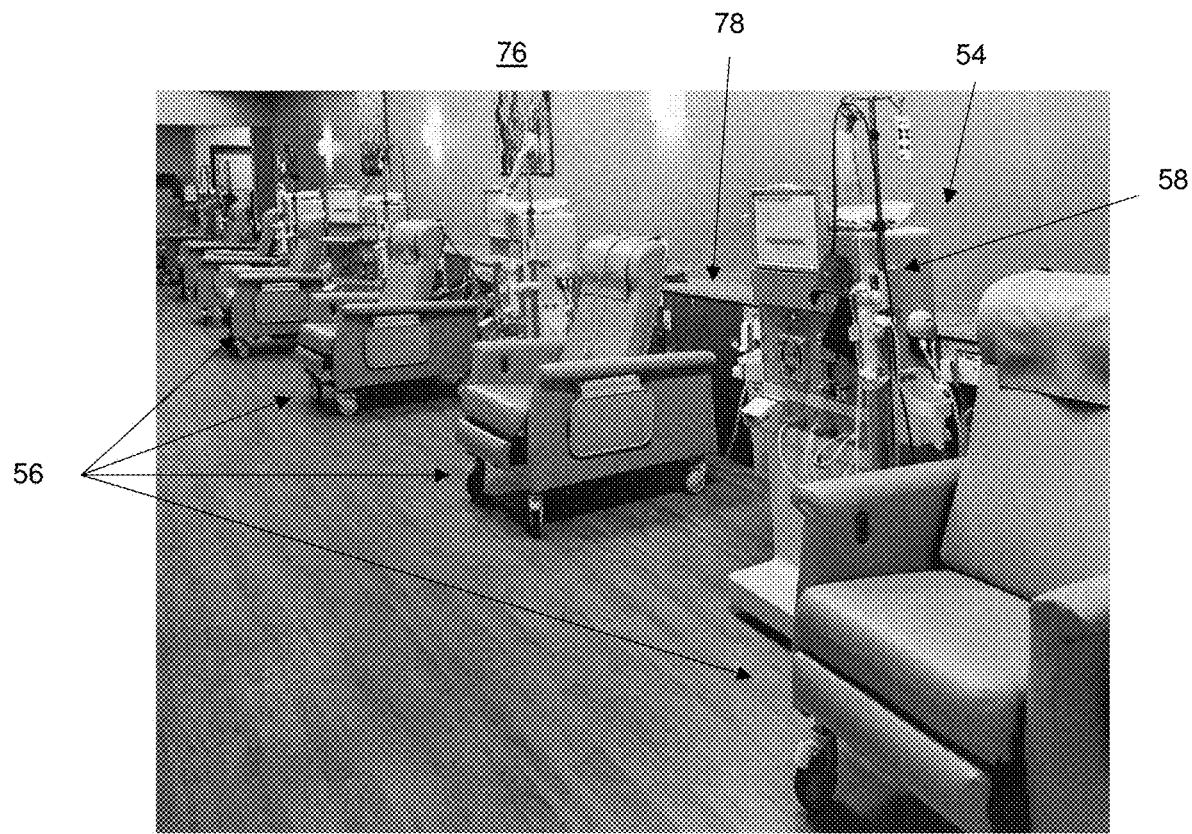
FIG. 5 is a perspective view of a kidney dialysis center having multiple dialysis units linked to exemplary indirect drain flush systems for dialysis effluent.

Referring to FIG. 5, an exemplary kidney dialysis center 76 having multiple kidney dialysis units 54 comprising chairs 56, and hemodialysis machines 58 linked to one or more exemplary drain systems (maintained within and hidden by chase cabinetry 78) is shown. In certain preferred embodiments, a single exemplary drain system serves four to six dialysis units 54.

Figure 6:
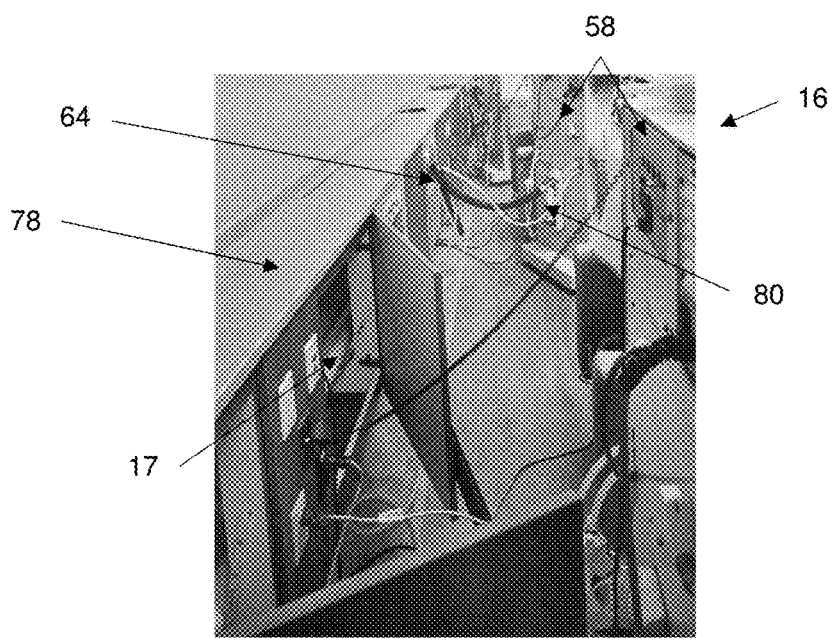
FIG. 6 is a rear perspective view of multiple dialysis units of the FIG. 3 embodiment.

As shown in FIG. 6, hemodialysis machines 58 of kidney dialysis units 16 are linked to the exemplary drain system 17 by an effluent hose 64. In the embodiment shown, the effluent hose 64 is connected to the hemodialysis machine 58 at the lower, rear portion 80 of the machine 58. The exemplary drain system 17 is maintained within chase cabinetry 78. In certain preferred embodiments, the drain system 17 is 15-25 feet long.

Figure 7:
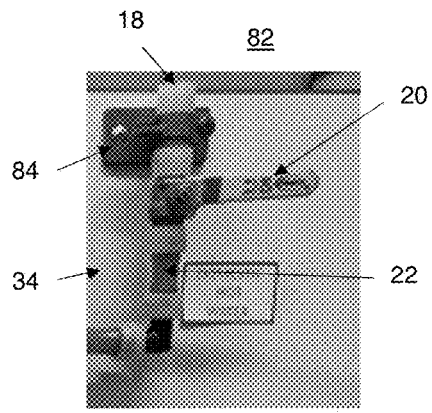
FIG. 7 is a front perspective view of an exemplary domestic hot water input of the FIG. 2 embodiment.

In the exemplary embodiments shown and described herein, the source of heated water is one or more domestic hot water tanks (not shown). Referring now to FIG. 7, an exemplary domestic hot water input 82 of the FIG. 2 embodiment is shown. The domestic hot water input 82 permits the flow of heated water 18 from the domestic hot water tanks (not shown) to a water cycler (not shown) by hot water pipes 22. A ball valve 20 may allow a user to permit or restrict the flow of heated water 18 to the water cycler (not shown). In this particular embodiment, the hot water pipes 22 are affixed to the wall 34 using fastened rigid straps 84. Additionally, in this particular embodiment, the temperature of the heated water 18 is approximately the internal temperature of the domestic hot water tanks (not shown). The present invention is not intended to be limited to the use of domestic hot water tanks for supplying heated water 18. For example, in other embodiments, the temperature of the heated water 18 can be controlled or altered after the water is discharged from a supply tank (not shown). In exemplary embodiments, the temperature of the heated water 18 is between 99° F. and 211° F.

Figure 8:
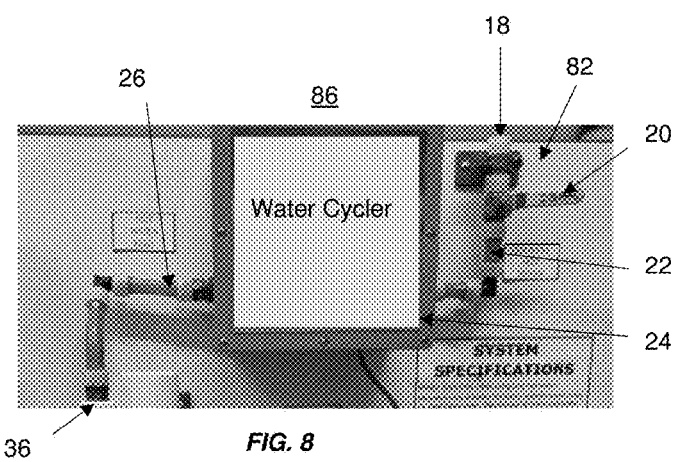
FIG. 8 is a front perspective view of an exemplary time-cycled hot water system of the FIG. 2 embodiment.

As shown in FIG. 8, an exemplary time-cycled hot water system 86 comprises a domestic hot water input 18 having hot water pipes 22 and ball valve 20, a water cycler 24, and a hot water feed 26. The water cycler 24 may control the volume and flow rate of heated water 18 discharged into the hot water air gap 36. In certain preferred embodiments, the water cycler discharges several gallons of heated water 24 into the hot water feed 26 every five minutes. It will be apparent to one of ordinary skill in the art that the heated water 18 volume discharged, flow rate and discharge time intervals can be varied without departing from the scope of the present invention. For example, the heated water 18 volume discharged and flow rate can be increased, and the discharge time intervals can be decreased when additional patients are being treated by dialysis units linked to the drain system in order to increase the amount of heated water 18 being mixed with the increased amount of dialysis effluent. Additionally, it will be apparent to one of ordinary skill in the art that timed discharge intervals are not always required to carry out the present invention. For example, in some embodiments, flow sensors in the dialysis waste line may determine when hot water is introduced to the dialysis waste line through a hot water air gap 36.

Figure 9:
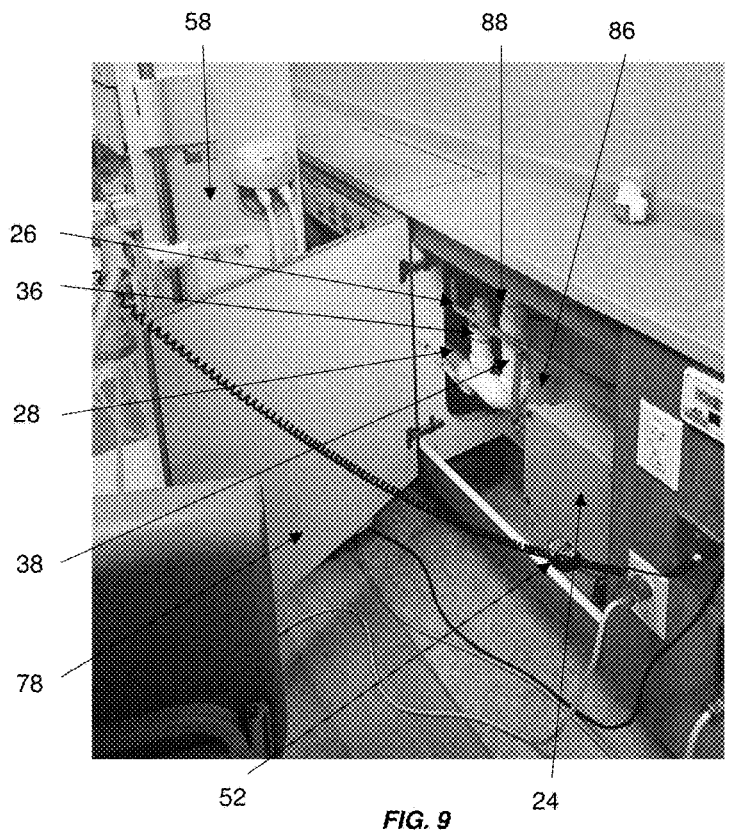
FIG. 9 is a perspective view of an exemplary indirect drain flush system of the FIG. 4 embodiment.

FIG. 9 shows an exemplary drain system 88 of the FIG. 4 embodiment, the drain system 88 comprising a time-cycled hot water system 86 having a water cycler 24 and hot water feed 26, alarm 52, hot water air gap 36, and a dialysis waste line 28 fed with dialysis effluent from the hemodialysis machine 58, the dialysis waste line 28 including an air admittance pipe 38. In this particular embodiment, the drain system 88 is maintained within chase cabinetry 78. Additionally, in this embodiment dialysis effluent enters (entry point not shown) the dialysis waste line 28 downline from the hot water air gap 36, and the dialysis effluent flows horizontally toward a release gap (not shown) for a length of space in the dialysis waste line 28 as the water cycler 24 discharges heated water. The heated water may flow through the hot water feed 26 to the hot water air gap 36, and after passing through the hot water air gap 36 and entering the dialysis waste line 28, the heated water may flow down the dialysis waste line 28 and mix with dialysis effluent.

Figure 10:
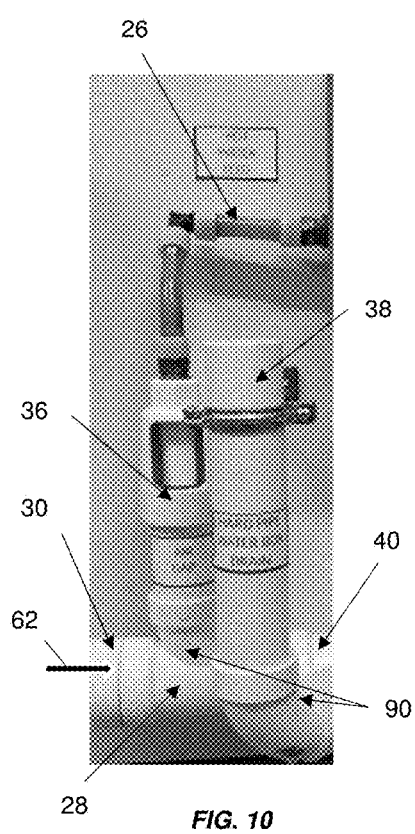
FIG. 10 is a front perspective view of a hot water feed, hot water air gap, and air admittance pipe of the FIG. 2 embodiment.

Referring now to FIG. 10, a dialysis waste line 28 including an air admittance pipe 38, hot water feed 26 and hot water air gap 36 of the FIG. 2 embodiment are shown. In this particular embodiment, spent dialysate 62 flows from the raw effluent zone 30 to the mixed effluent zone 40 past the hot water air gap 36. The hot water air gap 36 and the air admittance pipe 38 are attached to the main dialysis waste line pipe 28 by 90° elbow pipes 90.

Figure 11:
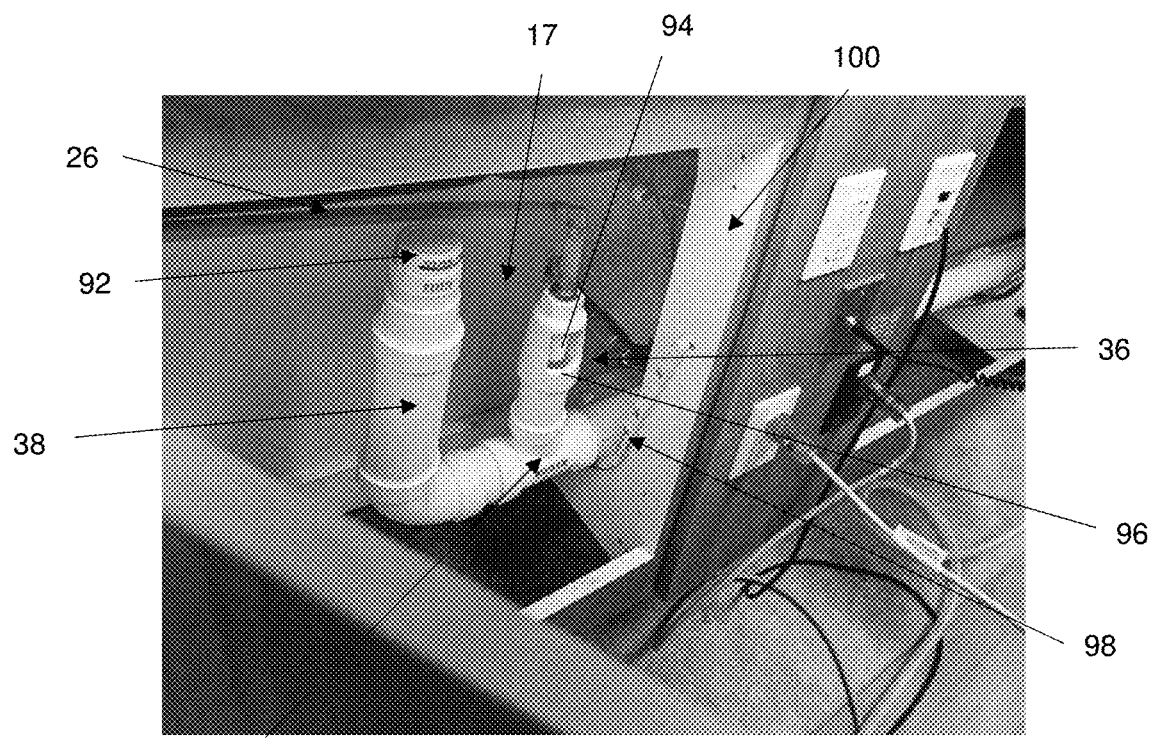
FIG. 11 is a perspective view of an exemplary indirect drain flush system of the FIG. 6 embodiment.

FIG. 11 shows an exemplary drain system 17 of the FIG. 6 embodiment. Heated water from the hot water feed 26 may be discharged through a splash guard 94 of the hot water air gap 36 into a basin opening 96 of the dialysis waste line 28. The bottom of the splash guard 94 may be positioned above the basin opening 96 of the dialysis waste line 28 to prevent any backflow from the dialysis waste line 28 from contaminating the potable water source supplying the heated water. Here, microorganisms and other potential contaminants from the spent dialysate are isolated from the hot water feed 26 by a vertical space between the splash guard 94 and basin opening 96. Pipes and fixtures containing potable water are therefore isolated from pipes and fixtures containing non-potable fluids, thus meeting fundamental plumbing specifications. It is not intended that the present invention be limited to the use of potable water for the heated water supply. It is further not intended that the present invention be limited to the use of splash guards. It will be apparent to one of ordinary skill in the art that any number of configurations for a hot water air gap may be employed without departing from the scope of the invention.

The dialysis waste line 28 may include an air admittance valve 92 at the top of the air admittance pipe 38. The air admittance valve 92 may prevent the buildup of negative pressure in the dialysis waste line 28. Negative pressure may occur when effluent displaces air in front of it as it travels through pipes, creating a vacuum when new air is not introduced to replace the displaced air. Negative pressure may cause backflow, such as backflow through the basin opening 96 of the hot water air gap 36, or may otherwise alter the flow path or flow rate of effluent in the dialysis waste line 28 if not addressed. Thus, the air admittance valve 92 may act to equalize the pressure in the dialysis waste line 28 by drawing in external air to replace displaced internal air. Specifically, when negative pressure begins to build up in the dialysis waste line 28, the air admittance valve 92 may be opened by the pressure gradient. External air may then be drawn through the opened air admittance valve 92 down the air admittance pipe 38 and into the main dialysis waste line pipe 28. Once the pressure has been equalized in the dialysis waste line 28, the air admittance valve 92 may close, preventing the escape of potentially odorous gases into the dialysis center. The air admittance pipe 38 may be positioned vertically so that the force of gravity may act perpendicular to the air admittance valve 92 to close it when pressure has been equalized in the dialysis waste line 28. In the embodiments shown and described herein, the flow of spent dialysate and mixed effluent towards the release gap (not shown) is also driven by the force of gravity.

The dialysis waste line 28 of the FIG. 11 embodiment is secured to chase cabinetry walls 100 by fastened J-hooks 98. The present invention is not intended to be limited to the use of chase cabinetry or fastened J-hooks for securing pipes and other fixtures. For example, referring back to FIG. 2, pipes are affixed to the wall 34 using fastened rigid straps 32. It will be apparent to one of ordinary skill in the art that there are various ways to secure pipes and fixtures of the present invention in a dialysis treatment center.

Figure 12:
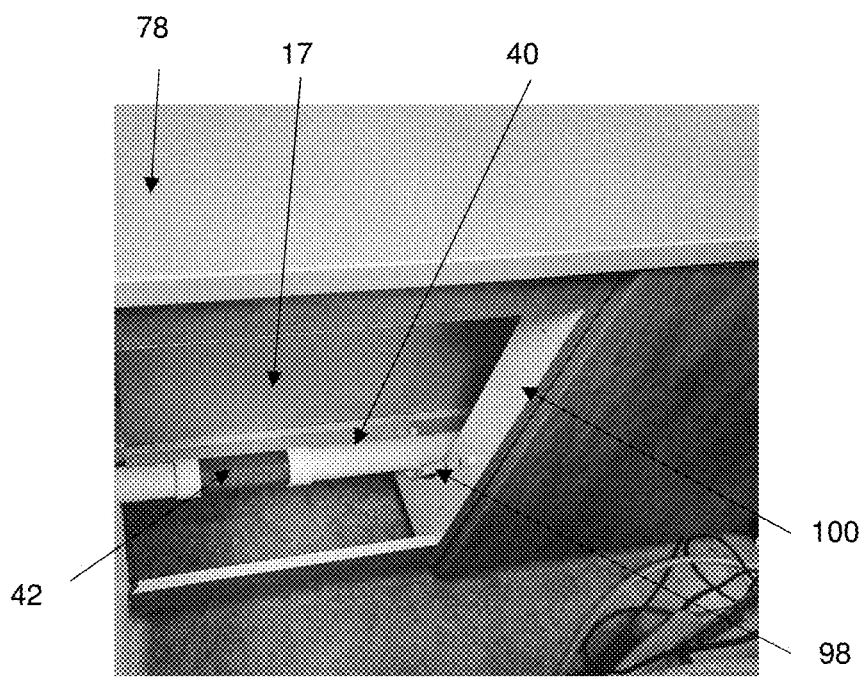
FIG. 12 is a perspective view of a mixed effluent pipe of the FIG. 11 embodiment.

Referring now to FIG. 12, a mixed effluent pipe 40 of the exemplary drain system 17 of the FIG. 11 embodiment is shown in chase cabinetry 78. In certain preferred embodiments, the mixed effluent pipe 40 comprises PVC. In this particular embodiment, the mixed effluent pipe 40 is secured to the chase cabinetry wall 100 by a fastened J-hook 98. The mixed effluent pipe 40 may include a section of transparent piping, or "inspection tubing" 42. The inspection tubing 42 may permit onlookers to determine if mixed effluent is flowing properly within the mixed effluent pipe 40. It will be apparent to one of ordinary skill in the art that inspection tubing 42 may be used for other pipe sections of the exemplary drain system 17 to ensure that spent dialysate and mixed effluent is flowing properly.

Figure 13:
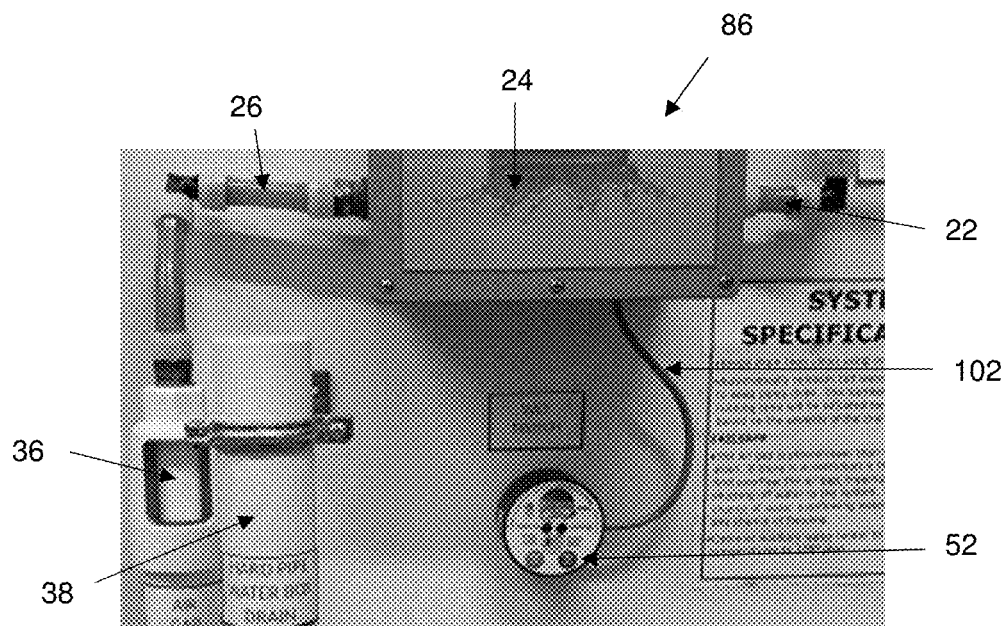
FIG. 13 is a front perspective view of a time cycled hot water system, hot water air gap, air admittance pipe, and alarm of the FIG. 2 embodiment.

Referring now to FIG. 13, the time-cycled hot water system 86 including hot water pipes 22, water cycler 24 and hot water feed 26, hot water air gap 36, air admittance pipe 38, and alarm 52 of the FIG. 2 embodiment are shown. The alarm 52 may be linked 102 to a flow meter and/or pressure gage (not shown) in the water cycler 24, wherein the flow meter and/or pressure gage may be configured to measure pressure and/or flow characteristics, and communicate the pressure and/or flow characteristics to at least one processor (not shown). The at least one processor may be configured to cause the alarm to provide an alert when measured pressure and/or flow characteristics are consistent with backup, fouling, lack of water input, or the like ("flow issues"). In other preferred embodiments, one or various components of an exemplary indirect drain flush system may be linked to at least one flow meter and/or pressure gage in communication with at least one alarm, which may alert system users if there are flow issues within one or various components of the indirect drain flush system. The alarm 52 may be configured to provide one or more alerts to notify a user when a flow issue has occurred, thus notifying the user that adjustments to the system may be required to resolve the flow issue.

Figure 14:
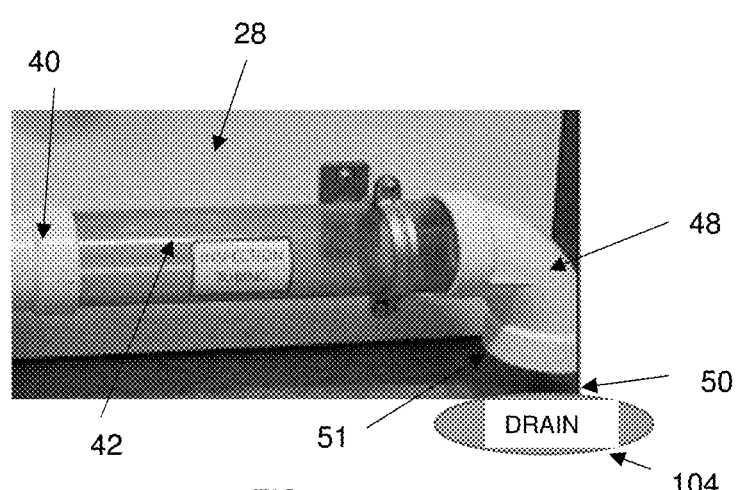
FIG. 14 is a front perspective view of various features of the FIG. 2 embodiment and a drain for receiving mixed effluent.

Referring now to FIG. 14, the mixed effluent zone 40 and inspection tubing 42 of the FIG. 2 embodiment are shown. In this particular embodiment, mixed effluent travels through the mixed effluent zone 40 towards an elbow pipe 48 directing the mixed effluent to the release gap 50 over a drain 104. The drain 104 may permit the mixed effluent discharged from the release opening 51 through the release gap 50 to enter a municipal sewage system, where fatty substances from the spent dialysate may remain suspended in wastewater before reaching a wastewater treatment facility (not shown). In the embodiment shown, the release gap 50 isolates the drain 104 from the dialysis waste line 28, thus preventing organisms, including microorganisms, or other contaminants, such as contaminants from backflow from the municipal sewage system, from infiltrating the dialysis waste line 28.

In certain preferred embodiments of the present invention, the aforementioned pipes and fixtures are temporarily suspended from, affixed or attached to walls or chase cabinetry in the dialysis center to define a portable indirect drain flush system. Referring back to FIGS. 6 and 9, by way of example and not limitation, the dialysis waste line 28 may be temporarily connected to the effluent hose 64. The time cycled-hot water system 86 may be temporarily attached to a domestic hot water supply. Additionally, the various component parts may easily be transported between different dialysis treatment centers and reassembled into an operational indirect drain flush system. Exemplary portable indirect drain flush systems may be beneficial for emergency scenarios where, for example, space in permanent dialysis centers is limited.

It will be appreciated by those skilled in the art that the present invention can be embodied in other specific forms without departing from the spirit or essential characteristics thereof. The presently disclosed embodiments are considered in all respects to be illustrative and not restricted. The scope of the invention is indicated by the appended claims rather than the foregoing description and all the changes that come within the meaning and range and equivalence thereof are intended to be embraced therein.

We claim:

1. An indirect drain flush system for dialysis effluent comprising:
    a dialysis waste line comprising a spent dialysate input configured for connection to a spent dialysate source, a heated water input configured for receiving heated water from a heated water supply, and a release opening;
    a water cycler;
    a heated water air gap positioned between the water cycler and the dialysis waste line; and
    an air admittance valve;
    wherein the water cycler is configured to cause heated water to be discharged through the heated water air gap into the heated water input of the dialysis waste line;
    wherein the spent dialysate input is configured to allow spent dialysate to enter the dialysis waste line and mix with heated water to form mixed effluent;
    wherein the air admittance valve is configured to regulate pressure in the dialysis waste line; and
    wherein the release opening is configured to cause mixed effluent to be discharged over at least one drain.

2. The indirect drain flush system of claim 1 further comprising:
    inspection tubing positioned at a portion of the dialysis waste line.

3. The indirect drain flush system of claim 1, wherein:
    the air admittance value is positioned on a substantially vertically oriented air admittance pipe.

4. The indirect drain flush system of claim 1, further comprising:
    an alarm in communication with at least one selected from the group of a flow meter, pressure gage, and combinations thereof, wherein the alarm is configured to provide an alert when a flow issue is detected.

5. The indirect drain flush system of claim 1, wherein:
    the water cycler is configured to cause heated water to be discharged through the heated water air gap into the heated water input of the dialysis waste line based on timed intervals.

6. The indirect drain flush system of claim 1, wherein:
    the heated water input is positioned upstream of the spent dialysate input.

7. The indirect drain flush system of claim 1, wherein:
    the heated water input is positioned downstream of the spent dialysate input.

8. The indirect drain flush system of claim 5, wherein:
    the water cycler is configured to cause at least one gallon of heated water per each dialysis unit linked to the indirect drain flush system to be discharged through the heated water air gap into the heated water input of the dialysis waste line approximately every 5 minutes during dialysis.

9. An indirect drain flush system for dialysis effluent comprising:
    a portable dialysis waste line configured to be temporarily linked to at least one dialysis unit, the portable dialysis waste line comprising a spent dialysate input configured for connection to a spent dialysate source, a heated water input configured for receiving heated water from a heated water supply, and a release opening;
    a water cycler;
    a heated water air gap positioned between the water cycler and the portable dialysis waste line; and
    an air admittance valve;
    wherein the water cycler is configured to be temporarily linked to the heated water supply, and is further configured to cause heated water therefrom to be discharged through the heated water air gap into the heated water input of the portable dialysis waste line;
    wherein the spent dialysate input is configured to allow spent dialysate from the at least one dialysis unit to enter the portable dialysis waste line and mix with heated water to form mixed effluent;
    wherein the air admittance valve is configured to regulate pressure in the dialysis waste line; and
    wherein the release opening is configured to cause mixed effluent to be discharged over at least one drain.

10. The indirect drain flush system of claim 9, further comprising:
    inspection tubing positioned at a portion of the dialysis waste line.

11. The indirect drain flush system of claim 9, further comprising:
    an alarm in communication with at least one selected from the group of a flow meter, pressure gage, and combinations thereof, wherein the alarm is configured to provide an alert when a flow issue is detected.

12. The indirect drain flush system of claim 9, wherein:
    the water cycler is configured to cause heated water to be discharged through the heated water air gap into the heated water input of the dialysis waste line based on timed intervals.

13. The indirect drain flush system of claim 9, wherein:
    the heated water input is positioned upstream of the spent dialysate input.

14. The indirect drain flush system of claim 9, wherein:
    the heated water input is positioned downstream of the spent dialysate input.

15. The indirect drain flush system of claim 9, wherein:
    the portable dialysis waste line is configured to be temporarily connected to an effluent hose.

16. A method for transporting dialysis effluent from a dialysis unit to a drain, the method comprising:
    providing a dialysis waste line comprising a spent dialysate input configured for connection to a spent dialysate source, a heated water input configured for receiving heated water from a heated water supply, and a release opening;
    providing a water cycler;
    providing a heated water air gap positioned between the water cycler and the dialysis waste line; and
    providing an air admittance valve;
    causing the water cycler to permit heated water to be discharged through the heated water air gap into the heated water input of the dialysis waste line;
    causing the spent dialysate input to permit spent dialysate to enter the dialysis waste line and mix with heated water to form mixed effluent;
    causing the air admittance valve to regulate pressure in the dialysis waste line; and causing the release opening to permit discharge of mixed effluent into at least one drain.

17. The method of claim 16 further comprising:
providing inspection tubing positioned at a portion of the dialysis waste line.

18. The method of claim 16, further comprising:
providing an alarm in communication with at least one selected from the group of a flow meter, pressure gage, and combinations thereof, wherein the alarm is configured to provide an alert when a flow issue is detected.

19. The method of claim 16, wherein:
the heated water input is positioned upstream of the spent dialysate input.

20. The method of claim 16, wherein:
the heated water input is positioned downstream of the spent dialysate input.

* * * * *